United States Patent [19]

Morman et al.

[11] Patent Number: 4,655,760
[45] Date of Patent: Apr. 7, 1987

[54] ELASTICIZED GARMENT AND METHOD OF MAKING THE SAME

[75] Inventors: Michael T. Morman, Alpharetta, Ga.; Tony J. Wisneski, Kimberly, Wis.

[73] Assignee: Kimberly-Clark Corporation, Neenah, Wis.

[21] Appl. No.: 760,438

[22] Filed: Jul. 30, 1985

[51] Int. Cl.$^4$ ............................................. A61F 13/16
[52] U.S. Cl. ............................................. 604/385 A
[58] Field of Search ................. 604/385.1, 385.2, 358; 156/183, 229, 224

[56] References Cited

U.S. PATENT DOCUMENTS

| | | |
|---|---|---|
| 1,544,312 | 6/1925 | Gray . |
| 1,911,227 | 5/1933 | Galligan . |
| 2,022,852 | 12/1935 | Galligan . |
| 2,030,746 | 2/1936 | Galligan . |
| 2,125,495 | 8/1938 | French . |
| 2,343,374 | 3/1944 | Hargreaves . |
| 2,604,097 | 7/1952 | White . |
| 2,905,581 | 9/1959 | Maxey . |
| 2,957,512 | 10/1960 | Wade . |
| 3,236,238 | 2/1966 | Morse . |
| 3,236,718 | 2/1966 | Cohn . |
| 3,316,136 | 4/1967 | Pufahl . |
| 3,468,748 | 9/1969 | Bassett . |
| 3,481,337 | 12/1969 | Ruffo . |
| 3,570,493 | 3/1971 | Olsson . |
| 3,622,434 | 11/1971 | Newman . |
| 3,639,917 | 2/1972 | Althouse . |
| 3,644,157 | 2/1972 | Draper . |
| 3,673,026 | 6/1972 | Brown . |
| 3,687,797 | 8/1972 | Wideman . |
| 3,692,603 | 9/1972 | Rhodes . |
| 3,842,832 | 10/1974 | Wideman . |
| 3,849,241 | 11/1974 | Butin . |
| 3,868,729 | 3/1975 | Lynam . |
| 4,014,338 | 3/1977 | Scharr . |
| 4,050,462 | 9/1977 | Woon . |
| 4,081,301 | 3/1978 | Buell . |
| 4,100,324 | 7/1978 | Anderson . |
| 4,209,563 | 6/1980 | Sisson . |
| 4,297,157 | 10/1981 | Van Vliet . |
| 4,305,990 | 12/1981 | Kelly . |
| 4,323,070 | 4/1982 | Ternstrom . |
| 4,333,782 | 6/1982 | Pieniak . |
| 4,340,563 | 7/1982 | Appel . |
| 4,379,016 | 4/1983 | Stemmler . |
| 4,397,645 | 8/1983 | Buell . |
| 4,413,623 | 11/1983 | Pieniak . |
| 4,418,123 | 11/1983 | Bunnelle . |
| 4,430,086 | 2/1984 | Repke . |
| 4,446,189 | 5/1984 | Romanek . |
| 4,450,026 | 5/1984 | Pieniak . |
| 4,525,407 | 6/1985 | Ness . |
| 4,543,099 | 9/1985 | Bunnelle . |

FOREIGN PATENT DOCUMENTS 2260716  5/1974  Fed. Rep. of Germany .

Primary Examiner—John D. Yasko
Attorney, Agent, or Firm—Joseph P. Harps

[57] ABSTRACT

Garments having a medial section which includes a gathered crotch portion and transversely opposed side sections are made by stretching an elastic layer transversely of the garment and stretch-bonding it to a gatherable non-elastic layer. Upon release of the elongating forces, the medial portion of the resulting composite contracts to form gathers and provides an elasticized portion which enhances fit and comfort of the garment. The elastic material may be liquid-impervious and the non-elastic material may be breathable whereby the medial portion of the garment, which may comprise a disposable diaper or panty, is rendered leak-proof or at least leak-resistant and the side portions are breathable for enhanced comfort. A method for making the garment comprises stretching the elastic material transversely to elongate it and maintaining it in its transversely elongated condition while bonding it by any suitable means to the gatherable non-elastic material.

23 Claims, 5 Drawing Figures

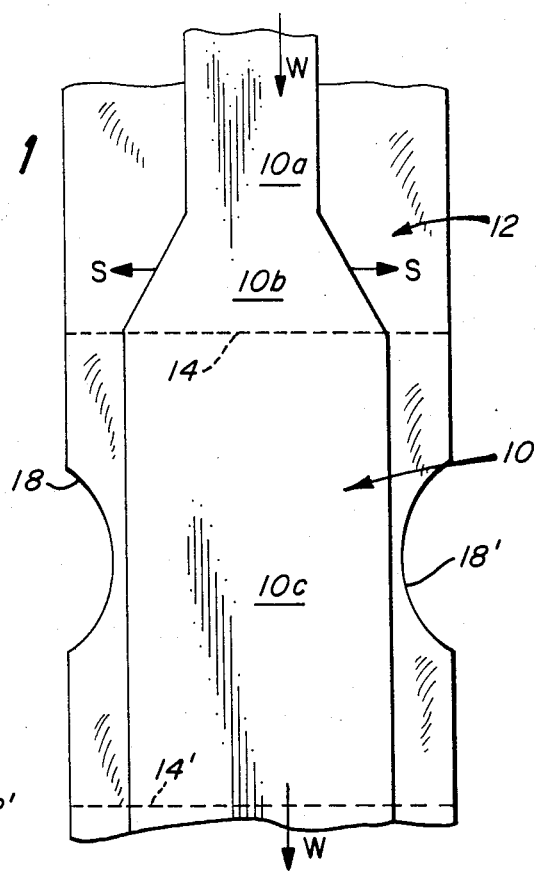
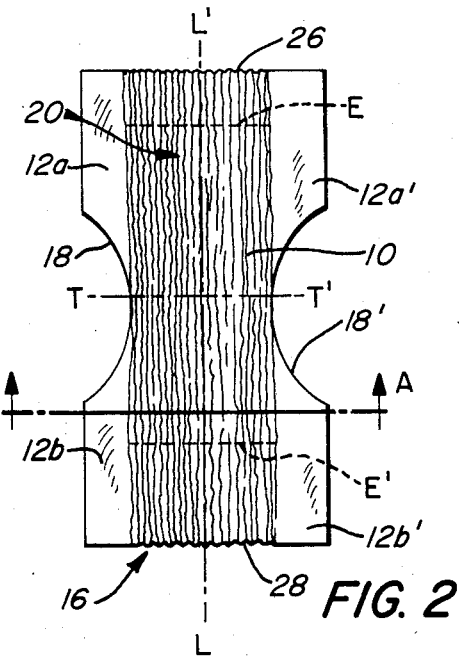
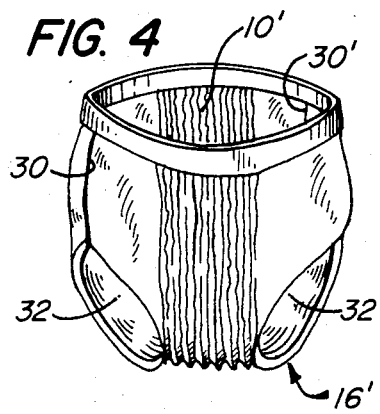
FIG. 4
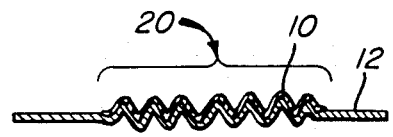
FIG. 2A
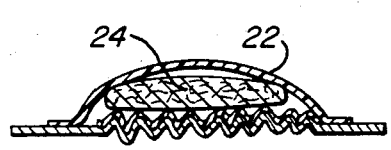
FIG. 3

ELASTICIZED GARMENT AND METHOD OF MAKING THE SAME

BACKGROUND OF THE INVENTION

1. Field Of the Invention

The present invention is concerned with an elasticized garment which is well suited for use as an incontinence control garment, such as a diaper, and more particularly as a disposable diaper. The present invention is in particular concerned with an elasticized garment in which the elastic layer is stretch-bonded to an outer cover.

2. Description Of The Related Art

Composite fabrics comprising at least one layer of nonwoven textile fabric mechanically secured to an elastic layer are known. For example, U.S. Pat. No. 4,446,189 discloses laminate materials comprising an inner layer of elastic material, needle punched at a plurality of locations to a nonwoven textile fabric layer. The superposed layers are then stretched to permanently stretch the nonwoven fabric. The nonwoven fabric layer is stated to exhibit increased bulk by virtue of the relaxation of its permanently stretched fibers.

U.S. Pat. No. 3,316,136 discloses a composite fabric comprising a layer of an elastic or resilient material and an overlying layer of fabric, for example, a woven fabric. The elastic fabric may be a polyurethane foam or a nylon woven to impart stretchability or the like and, as disclosed in the paragraph bridging columns 1 and 2 of the patent, an adhesive may be applied in a predetermined pattern to the elastic material which is then stretched, and while in a stretched or elongated state, the overlying fabric is contacted therewith and held in pressure engagement for a time sufficient to ensure adhesion of the two layers. When the applied adhesive is dry, tension on the backing material is released causing the overlying non-elastic fabric to gather in the areas outlined by the adhesive.

U.S. Pat. No. 3,687,797 discloses the manufacture of a resilient cellulosic wadding product attained by laminating paper and a prestretched polyurethane foam material. An adhesive is applied in a desired pattern as illustrated in the drawings and the paper is laminated to either side of the prestretched polyurethane foam material. The paper layers may be wetted to reduce their resistance to compression by retraction of the prestretched polyurethane foam after lamination of the paper layers thereto, thereby providing a creped effect as illustrated in FIGS. 3 and 4 of the patent.

U.S. Pat. No. 4,323,070 discloses a disposable diaper construction in which a series of elastic bands or threads extend transversely of the diaper in order to impart a bowl-like shape to the central or crotch portion of the diaper. U.S. Pat. No. 4,430,086 shows a diaper construction in which transversely disposed elasticized waistbands are utilized to provide a bowed or bowl-like configuration to the diaper.

U.S. Pat. No. 3,481,337 discloses a corrugated diaper having longitudinally extending corrugations preferably formed across the entire transverse width of the diaper. The corrugations may be held in place by glue dots (item 15 in FIG. 3) or by stitching.

U.S. Pat. No. 2,604,097 discloses a child's training panty comprising a fabric backing sheet 11, 12 and an absorbent pad 24 between which a plastic lining 27 is disposed to cover generally the medial portion of the panty.

SUMMARY OF THE INVENTION

In accordance with the present invention there is provided a garment comprising a medial section between transversely opposed side sections, the medial section having a gathered crotch portion and the garment being comprised of a gatherable first layer (which is optionally liquid-pervious and breathable and optionally non-elastic) and an elastic second layer (which is optionally liquid-impervious) stretch-bonded to the first layer to overlie at least the crotch portion of the garment to define an elasticized, gathered portion of the garment.

In one aspect of the invention, the elasticized, gathered portion of the garment is extensible and contractible in a direction which is transverse of the garment, preferably, in a direction which is perpendicular to the longitudinal axis of the garment.

Other aspects of the invention provide one or more of the following features: the elastic second layer, which may be a film or a fibrous material, may overlie substantially the entire crotch portion; the crotch portion may be defined between transversely opposed leg-cut-outs and the transversely-opposed side sections may each comprise a pair of side sub-sections respectively disposed on longitudinally opposite sides of their associated leg cut-out; the elastic second layer may extend beyond the crotch portion longitudinally of the garment; the elastic second layer may be stretch-bonded to the gatherable first layer at a plurality of spaced-apart locations in a repeating pattern with the gatherable first layer gathered between the bonded locations; a liquid-pervious, breathable third layer may overlie the elastic second layer to provide a laminate in which the elastic second layer is sandwiched between the third layer and the first layer; and the garment, which may be an open, wrap-around diaper or a closed, slip-on panty in two of its embodiments, may further include an absorbent layer interposed between the third layer and the elastic second layer.

Method aspects of the invention are provided by a method of producing a garment having a medial section which includes a gathered crotch portion and is disposed between transversely opposed side sections, the method comprising: stretching an elastic second layer to elongate it, preferably about 10% to 600%, more preferably about 50% to 300%, of its relaxed length, maintaining the elastic second layer in its elongated condition while bonding it to a gatherable, optionally non-elastic, first layer with the direction of elongation of the elastic layer positioned transversely of the garment to form a bonded composite material overlying at least the crotch portion of the garment; and relaxing the bonded composite material whereby to gather the gatherable, non-elastic first layer and form the gathered crotch portion.

BRIEF DESCRIPTION OF THE DRAWINGS

FIG. 1 is a schematic plan view illustrating the bonding of two webs of material to form an article comprising an embodiment of the present invention;

FIG. 2 is a schematic plan view showing one embodiment of an article of the invention in a relaxed condition;

FIG. 2A is a cross-section view in elevation taken along line A—A of FIG. 2;

FIG. 3 is a view corresponding to FIG. 2A showing a diaper embodiment of the present invention; and FIG. 4 is a schematic perspective view showing a panty garment comprising an embodiment of the present invention.

DESCRIPTION OF THE PREFERRED EMBODIMENTS

The garments of the invention generally comprise at least one layer of elastic material bonded to at least one other layer of gatherable, non-elastic material, the elastic layer being maintained in a stretched condition within its elastic range during the bonding step so that upon contracting or recovering after release of the elongating tension force, the layer or layers to which it is bonded will gather or pucker. The direction of elongation of the elastic layer is positioned transversely, preferably perpendicularly, to the longitudinal center line of the garment to provide a gathered, elasticized medial portion of the garment. As used herein and in the claims, the following terms have the stated meanings: "transversely" of the garment means a direction extending side-to-side, i.e., hip to hip to the wearer; the "longitudinal axis" of the garment is the front-to-rear center line of the garment; and "stretch-bonded" with reference to the elastic, second layer means that the elastic layer is bonded to the first, gatherable layer while the elastic layer is maintained in an elongated condition relative to its relaxed length. As described in more detail below, the gathered, elasticized medial portion of the garment provides a more conformable garment, such as a diaper or panty. The elastic layer used to gather the medial portion may be made of a liquid-impervious material in order to provide enhanced liquid retention in the medial portion of the garment, which includes the crotch portion. Therefore, the construction of the garment of the invention is particularly adapted for incontinence control garments such as diapers or panties, and because of its relatively low cost of construction is well adapted for the construction of disposable diapers or panties. The first, preferably outer, layer to which the elastic layer is bonded is preferably non-elastic and therefore serves to limit the degree of transverse stretch, which is desirable particularly with respect to modern methods of manufacturing disposable diapers and panties.

A wide variety of materials may be employed as the elastic layer. As used herein and in the claims, the term "elastic" has its usual broad meaning, which may be conveniently defined as meaning a material which is elongatable by at least 25% of its relaxed length, i.e., which by stretching may be elongated to at least one and one-quarter times its relaxed length (an elongation of 25%), and which will recover upon release of the stretching, i.e., tensioning, force at least 40% of its elongation. According to this definition, upon release of the tensioning force at 25% elongation, the material must recover to not more than about a 15% elongation. For example, under the foregoing definition a material is deemed to be elastic if a piece of it 100 centimeters ("cm") in length can be stretched to elongate it to a length of at least 125 cm and if, in the case of being stretched to 125 cm, upon release of the elongating force it recovers to a length of not more than about 115 cm. Of course, many elastic materials will be elongatable by much more than 25% of their relaxed length and many of these will recover to, or close to, their original relaxed length upon release of the tensioning force. This latter class of materials is generally preferred for purposes of the present invention. Elastic materials suitable for use in the invention include not only webs of elastic films, such as cast or blown films, but also nonwoven fibrous elastic webs such as, for example, meltblown elastomeric fibrous nonwoven webs. As used herein, "meltblown" microfibers refer to small diameter fibers, usually of a diameter not greater than about 100 microns, made by extruding a molten thermoplastic material as molten threads from a plurality of fine orifices and into a high velocity gas (e.g., air) stream which attenuates the threads of molten thermoplastic material to reduce the diameter thereof, the gas stream-borne fibers then being deposited upon a collecting screen to form a coherent nonwoven web of randomly dispersed fibers. Such a process is disclosed, for example, in U.S. Pat. No. 3,849,241, issued Nov. 19, 1974 to Robert R. Butin et al.

The fibrous elastic web may also comprise a composite material in that it may be comprised of two or more individual coherent webs or it may comprise one or more webs individually comprised of a mixture of elastic and non-elastic fibers. As an example of the latter type of elastic web, reference is made to the aforementioned U.S. Pat. No. 4,209,563 in which elastomeric and nonelastomeric fibers are co-mingled to form a single coherent web of randomly dispersed fibers. Another example of such a composite web would be one made by a technique such as disclosed in U.S. Pat. No. 4,100,324, issued July 11, 1978 to Richard A. Anderson et al, and assigned to the assignee of this application. That patent discloses a nonwoven material comprised of a mixture of meltblown thermoplastic and other fibers which are combined in the gas stream in which the meltblown fibers are borne so that an intimate entangled co-mingling of thermoplastic meltblown fibers and other, e.g., wood pulp or staple fibers, are co-mingled prior to being collected upon a collecting device to form a coherent web of randomly dispersed fibers. The subject matter of U.S. Pat. Nos. 4,209,563 and 4,100,324 is hereby incorporated by reference.

A useful material for making the elastomeric fiber of the fibrous nonwoven elastic web, most preferably for making meltblown elastomeric fibers, is a block copolymer having the general formula A-B-A' wherein A and A' are each a thermoplastic polymer end block or segment which includes a styrenic moiety such as a poly (vinylarene) and B is an elastomeric polymer midblock such as a conjugated diene or lower alkene. A preferred material is one in which the A and A' endblocks are selected from the group including polystyrene or polystyrene homologs and the B midblock is selected from the group including polybutadiene, polyisoprene or poly(ethylene-butylene). The A and A' end block may be the same. Materials of this general type are disclosed in U.S. Pat. No. 4,333,782, issued June 8, 1982 to H. A. Pieniak. Similar materials are disclosed in U.S. Pat. No. 4,418,123, issued Nov. 29, 1983 to William L. Bunnelle which describes A-B-A block copolymers having styrenic end blocks A and amorphous intermediate blocks B. Commercially available A-B-A' block copolymers having thermoplastic polystyrene end blocks or segments and a saturated or essentially saturated poly (ethylene-butylene) midblock B or segment, sometimes referred to as an S-EB-S polymers, are available under the trade designation KRATON G, for example, Kraton G-1650, Kraton G-1652 and Kraton GX-1657, from The Shell Chemical Company and may be employed in blended form with polyolefins as described in U.S. patent application Ser. No. 06/760,698 of M. T. Morman et al, entitled "Polyolefin-Containing Extrudable Compositions And Methods For Their Formation Into Elastomeric Products", the subject matter of which is hereby incorporated by reference, in preferred embodiments of the invention. However, any other suitable elastic fiber forming resin or elastic resin blend may be utilized in forming the elastic fibers of the fibrous nonwoven elastic web or for the elastic film. Other exemplary elastomeric materials for use in formation of fibrous nonwoven elastic webs or films in the practice of the invention include polyester elastomeric materials such as, for example, those available under the trade designation Hytrel from E. I. duPont DeNemours & Co., polyurethane elastomeric materials such as, for example, those available under the designation Estane from B. F. Goodrich & Co. and polyamide elastomeric materials such as, for example, those available under the trade designation Pebax from the Rilsan Company. Generally, any suitable elastomeric fiber forming resins or blends containing the same may be utilized for the nonwoven webs of elastomeric fibers of the invention and any suitable elastomeric film forming resins or blends containing the same may be utilized for the elastomeric films of the invention.

The elastomeric film or nonwoven web of elastomeric fibers may be made of a material which essentially consists of the elastomeric thermoplastic resin, which typically may contain plasticizers, pigments, antioxidants and other conventionally employed additives. Such an elastomeric fibrous nonwoven web and processes for forming the web are disclosed in U.S. patent application Ser. No. 06/760,366 in the name of M. T. Morman and T. J. Wisneski entitled "High Temperature Method of Making Elastomeric Materials and Materials Obtained Thereby". The subject matter of this application is hereby incorporated by reference. Alternatively, as disclosed in the aforesaid patent application of Michael T. Morman et al, entitled "Polyolefin-Containing Extrudable Compositions and Methods For Their Formation Into Elastomeric Products" elastomeric thermoplastic S-EB-S resins may be blended with polyolefins, e.g., polyethylene, polypropylene, polybutene or copolymers thereof, while still retaining desirable elastomeric properties of the finished fiber. Aside form the aforesaid KRATON G resins, other A-B-A' block copolymers may be utilized, such as S-I-S block copolymer resins having polystyrene or polystyrene homolog end blocks A and A' and polyisoprene as the midblock B, and S-B-S block copolymers having polystyrene or polystyrene homolog end blocks A and A' and polybutadiene as the B midblock. Polymers of these types are commercially available under the KRATON D trademark from Shell Chemical Company and under the Solprene 418 trademark of Philips Chemical Company.

Any suitable elastic film, as distinguished from an elastic nonwoven web of elastomeric fibers, may also be utilized in accordance with the invention. For example, elastic films sold under the trademark Polytrope by A. Schulman Corporation of Akron, Ohio, comprising a block copolymer of poly (cis-butadiene) and poly(t-butylmethacrylate) can be bonded to a non-elastic web such as a bonded carded web of fibers of polyethylene terephthalate. Any other suitable elastic film may be utilized as the elastic web of the garment of the present invention such as a film formed from a blend of a KRATON G block copolymer (in which the B mid-block is poly(ethylene-butylene)) and a polyolefin the manufacture of which is described in U.S. patent application Ser. No. 06/760,691 in the name of W. B. Haffner, M. T. Morman and T. J. Wisneski entitled "Block Copolymer Polyolefin Elastomeric Films". The subject matter of this application is hereby incorporated by reference. Inasmuch as it is a preferred and desirable feature that the elastic layer of the garment of the invention be liquid-impervious, imperforate webs or films rather than foraminous materials are preferred for utilization as the elastic layer in the garments of the invention. However, the liquid-imperviousness may be provided by a material other than the elastic layer so that the latter need not necessarily be liquid-impervious.

Whether the elastic layer comprises a film or a fibrous elastomeric material, it should have sufficient elasticity and be bondable to the non-elastic layer with sufficient strength to form a bonded composite which may be stretchable. In many cases, the elastic layer material does not exhibit a significant degree of adhesion to the gatherable web material, particularly when the elastic layer is held in an elongated condition while being bonded to the gatherable web or webs, so that an adhesive may be employed to bond the layers. However, it is often desired that the composite material should have a soft hand and feel so it may be desirable, at least in some cases, that the bonding of the elastic layer to the gatherable layer of the laminate be done either without an adhesive, as by heat bonding, ultrasonic welding or the like, or by using an amount and type of adhesive which will not make the resultant material unduly stiff. Suitable combinations of bonding techniques (heat, ultrasonic, adhesive, etc.) may be used. A preferred method of bonding the elastic layer in an elongated condition to the gatherable web or layer is that disclosed in U.S. patent application of J. D. Taylor et al, Ser. No. 06/760,437 entitled "Composite Elastomeric Material And Process For Making The Same", the disclosure of which is hereby incorporated by reference. The technique of the Taylor et al application involves relaxing the bonded materials immediately after the bonding step to avoid setting the elastic layer in the elongated condition and so diminishing or losing its elasticity. This technique is particularly useful with low basis weight elastic materials, e.g., those of a basis weight of from about 5 to 300, say, 10 to 200, grams per square meter. Such low basis weight materials are preferred in the practice of the invention at least for disposable articles, because of their lower cost as compared to heavier basis weight materials. However, the present invention also encompasses the use of heavier basis weight elastic materials, for example, up to 750 grams per square meter or higher.

Because the elastic layer may be bonded to a gatherable non-elastic layer, by which is meant generally any suitable material which lacks the characteristics of an elastic as defined above, the non-elastic layer has a limiting effect on the degree of stretch of the elastic layer. For example, if the elastic layer is stretched to an elongation of 100%, i.e., to twice its relaxed length, and then bonded at spaced-apart bonding locations to a non-elastic web such as a nonwoven spun-bonded polyolefin web, upon release of the stretching force acting on the composite material, puckers or gathers will form in the gatherable non-elastic layer between the bond locations as the composite material is contracted by recovery of the elongated elastic layer thereof. The production of spun-bonded nonwoven webs is illustrated in U.S. Pat. No. 4,340,563, issued July 20, 1982 to David W. Appel et al, and assigned to the assignee of this application. Generally, a thermoplastic material is extruded through a spinnerette and eduction drawn into filaments on a collecting or forming surface. By a "gatherable" web or material is meant one which can be pleated or gathered as described, by contraction of an elastic web which was bonded to the gatherable web while the elastic web was in an elongated, i.e., stretched, condition. When the composite material is stretched, the original length of the non-elastic layer limits the elongation of the composite material which is attainable without rupturing the gatherable web. The non-elastic web may thus be utilized as a "stop" to prevent further or excessive stretching of the composite material and therefore of the elastic web. Accordingly, the strength of the non-elastic web, which is usually much higher than that of the elastic material, particularly when the latter is a low basis weight material, generally determines the failure strength of the composite.

Referring now to FIG. 1, there is shown in plan view a web of elastic material 10 positioned above a web of non-elastic material 12 to which elastic material 10 is to be bonded. Webs 10 and 12 may, in the known manner, be supplied from respective storage rolls thereof (not shown) and brought into contact one with the other while moving at high speed, typically 4 to 500 feet per minute or more in the direction indicated by the arrows W in FIG. 1. The elastic web 10 is narrower than non-elastic web 12 as shown by section 10a, the width of which is the unelongated width of web 10. In section 10b of elastic web 10, stretching forces indicated by the arrows S are applied by known means, for example by a tenter frame or stretching rollers (neither of which is shown) and elastic web 10 is transversely elongated to its width illustrated in section 10c thereof. While web 10 is in the transversely elongated condition shown in section 10c thereof, webs 10 and 12 are bonded to each other by any conventional means. For example the two webs may be thermally bonded to each other, ultrasonically bonded to each other or bonded to each other by means of an adhesive or a combination of any of the foregoing. For example, thermal bonding may be effectuated by passing the overlaid webs into the pressure nip formed by a calender roller and an anvil roller, at least one of which is heated sufficiently to soften at least parts of one of the webs 10 and 12 sufficiently to enhance adherence of it to the other web. One or both of the rollers comprising the pressure nip may have an embossed pattern thereon so that the bonding may be applied in a repeating pattern with bonded sites or locations spaced apart one from the other to provide a repeating pattern of bonded locations interspersed by unbonded sections therebetween. After the two webs are bonded together they may be cut transversely along cutting lines 14, 14' to form discrete articles 16 (FIG. 2). Transversely opposed leg cut-outs 18, 18' may be made in web 12. FIG. 2 shows a transverse axis T—T' disposed perpendicularly to longitudinal axis L—L' of article 16.

The forces retaining web 12 and transporting it hold it in its flat stretched position indicated in FIG. 1 so that web 12 restrains transversely stretched elastic web 10 from returning to its unelongated or relaxed condition. However, upon cutting of discrete article 16 from the combined webs, the restraining forces thus imposed upon transversely stretched elastic web 10 are released and web 10 contracts resulting in the formation of puckers or gathers which extend longitudinally along discrete article 16 and contract the width of the discrete article 16 as compared to the width of web 12. As seen in FIG. 2, web 10 overlies a medial portion of article 16, defining a gathered, medial portion thereof. A comparison of FIGS. 1 and 2 shows that article 16 is narrower than web 12 from which it is formed. Gathered portion 20 of the resultant composite material is seen in cross-section in FIG. 2A and it will be appreciated that the transverse contraction provides a bulked, stretchable medial gathered portion 20 of article 16. Article 16 as illustrated in FIG. 2 may comprise a diaper, particularly a diaper which may be made inexpensively enough so that it may economically be disposed of after use, rather than being laundered and reused. For example, elastic web 10 may comprise an elastic web of any suitable material such as an elastic film or a nonwoven web of elastic fibers. Gatherable and non-elastic web 12 may preferably comprise a breathable material such as a spun-bonded polypropylene fiber fabric or the like.

The generally H-shaped configuration of article 16 will be recognized as the conventional configuration of a disposable diaper outer cover which may be supplied with fastening tapes, an absorbent pad and an inner cover as is conventional practice in the art, to comprise a disposable diaper. For example, FIG. 3 shows the composite of FIG. 2A to which has been bonded a liquid-pervious inner liner 22 which may be comprised of, for example, a spun-bonded polypropylene fiber material conventionally used for the inner liner of disposable diapers. An absorbent pad 24 may be sandwiched between inner liner 22 and the composite of FIG. 2A provided by the bonding of webs 10 and 12, so that, as is in the illustrated embodiment of FIG. 3, the composite of 2A is an outer cover of the disposable diaper construction of FIG. 3 and the liner 22 is the inner cover of the diaper of FIG. 3 and the absorbent pad 24 is retained between the inner and outer cover, as a result of the bonding of the inner liner 22 to the outer cover. In the embodiment of FIG. 3, absorbent pad 24 may be bonded to inner liner 22 to help retain pad 24 in place but it is not bonded to the outer cover provided by the composite of webs 10 and 12 so as to permit expansion and contraction of the latter to provide a smooth and comfortable fit on the wearer. By providing elastic web 10 of a liquid-impervious material, it serves as the leak resistant outer cover for the diaper.

The portion of non-elastic material 12 left uncovered by elastic material 10 comprises, as illustrated in FIG. 2, a first pair of side sub-sections 12a, 12b and a second pair of oppositely disposed side sub-sections 12a' and 12b'. The material of gatherable, non-elastic web 12 is preferably breathable, allowing the passage of moisture and air therethrough. This results in the side sections being breathable. For example, if non-elastic web 12 is made of a breathable spun-bonded polyolefin fiber material, the comfort of the wearer of the diaper formed therefrom is enhanced by permitting air circulation and some evaporative drying.

While it is a convenience in manufacturing articles from continuous webs of non-elastic and elastic material to have elastic material 10 of article 16 (FIG. 2) extend longitudinally coextensively with non-elastic web 12, such coextensivity is not necessary. Thus, with reference to the FIG. 2 embodiment, web 10 could terminate short of one or both of transverse edges 26, 28 of article 16 as indicated by the dotted lines E and E'. This latter construction would provide a breathable waistband area, front and back, when the diaper of FIG. 3 is placed upon the wearer in the conventional manner by being placed between the wearer's legs and folded transversely in the crotch region (generally along axis T—T' of FIG. 3) and fastening, for example, side sub-section 12a in overlapping engagement with side sub-section 12b and side sub-section 12a' in overlapping engagement with side sub-section 12b'. The article illustrated in FIG. 3 would comprise what may be described as an open, wrap-around garment, i.e., a diaper.

It will be appreciated that article 16 could be folded about its transverse axis T—T and the longitudinally extending edges of side sub-sections 12a and 12b joined together in a seam and similarly, the longitudinally extending edges of side-sub-sections 12a' and 12b' be joined in a seam. The result would be a panty construction which may be described as a closed, slip-on type garment.

FIG. 4 illustrates such a closed, panty construction in which the medial portion of the panty has an elastic web 10' providing a medial, elasticized portion of panty 16' which may be made from article 16 illustrated in FIG. 2, in which side sub-sections 12a and 12b are joined together along their longitudinal edges at respective side seams 30 and 30'. The leg cut-outs 18, 18' of FIG. 2 would thus be joined together to form respective circular or oval leg openings 32 and 32'. Obviously, panty 16' could further be provided with an inner layer and an absorbent pad analogous to inner layer 22 and absorbent pad 24 illustrated in FIG. 3.

The amount of elasticity of the composite material obtained by stretch-bonding the elastic layer to the non-elastic layer is readily controlled for given combination of materials by varying the amount of transverse elongation imposed on the elastic layer during bonding. It is also within the purview of the invention to elongate the elastic layer longitudinally, that is in the machine direction, or both transversely, that is in the cross-machine direction, and longitudinally to provide a selected degree of elasticity in both the machine and cross-directions of the resultant composite material and article. Being thus able to control the direction of elongation and contraction of the composite material is a useful feature not only in tailoring the properties of the finished article or garment but is often useful in handling and manipulating the composite material during manufacturing processes. Obviously, the basis weight and stiffness of the elastic layer and the non-elastic layer and the degree and direction of elasticity of the elastic layer may be selected to provide the desired properties in the finished composite material or article. Generally, the gatherable layer is stiffer and has greater tensile strength than the elastic layer bonded thereto. For example, the gatherable layer, although it may comprise any suitable woven textile or the like, for the sake of reducing costs will often comprise a nonwoven fabric such as a bonded carded web or a spun-bonded or melt-blown fiber nonwoven material. If it is desired to provide stretch in only one direction, the elastic layer is stretched only in one direction and not stretched in the other at the time of bonding so that upon release of the elongating tensioning forces the composite material contracts in only one direction and is elasticized in only one direction.

The elastic layer material such as the thermoplastic KRATON block copolymers described above are generally more expensive than the non-elastic, nonwoven fabrics typically used in the manufacture of disposable items. Because the tensile strength and tear strength of the composite material is determined by the tensile and tear strength of the usually less expensive and stronger nonwoven, non-elastic material the elastic layer need only be substantial enough to provide the desired degree of elasticity for the composite material. Therefore, the basis weight of the elastic layer may be reduced significantly relative to what it would be in an elastic fabric comprising only the elastic layer and need be sufficient only to provide the desired degree of elasticity in the composite layer.

This case is one of a group of cases which are being filed on the same date. The group includes application Ser. No. 06/760,449 in the name of M. T. Morman and entitled "Composite Nonwoven Elastic Web"; application Ser. No. 06/760,445 in the name of M. T. Morman entitled "Gathered Fibrous Nonwoven Web"; application Ser. No. 06/760,698 in the name of M. T. Morman and T. J. Wisneski entitled "Polyolefin-Containing Extrudable Compositions and Methods for Their Formation Into Elastomeric Products"; application Ser. No. 06/760,438 in the name of M. T. Morman and T. J. Wisneski entitled "Elasticized Garment and Method of Making the Same"; application Ser. No. 06/760,366 in the name of M. T. Morman and T. J. Wisneski entitled "High Temperature Method of Making Elastomeric Materials and Materials Obtained Thereby", application Ser. No. 06/760,437 in the name of M. J. Vander Wielen and J. D. Taylor entitled "Composite Elastomeric Material and Process for Making the Same", and application Ser. No. 06/760,691 in the name of William B. Haffner, Michael T. Morman and T. J. Wisneski entitled "Block Copolymer—Polyolefin Elastomeric Films". The subject matter of all of these applications is hereby incorporated by reference.

The garments of the invention, such as undergarments, incontinence control garments such as disposable diapers, and the like have a low cost relative to woven or knitted fabrics which permits their economic use in "disposable" articles, by which is meant articles, intended to be disposed of, rather than laundered and reused, after one use.

While the invention has been described in detail with respect to specific preferred embodiments thereof, it will be appreciated that upon a reading and understanding of the foregoing that numerous variations will occur to those skilled in the art which variations are believed to lie within the scope and spirit of the present invention and the appended claims.

What is claimed is:

1. A garment comprising a medial section disposed between transversely opposed side sections, the medial section having a gathered crotch portion and the garment being comprised of a gatherable first layer having an elastic second layer stretch-bonded thereto to overlie at least the crotch portion of the garment to define an elasticized, gathered portion of the garment.

2. The garment of claim 1 wherein the gatherable first layer is a non-elastic layer.

3. The garment of claim 1 wherein the elasticized, gathered portion of the garment is extensible and contractible in a direction transverse of the garment.

4. The garment of claim 3 wherein the gatherable first layer is a non-elastic layer.

5. The garment of claim 2 wherein the elastic second layer is a liquid-impervious material and overlies substantially the entire crotch portion.

6. The garment of claim 2 wherein the crotch portion is defined between transversely opposed leg cut-outs and the transversely-opposed side sections each comprise a pair of side sub-sections respectively disposed on longitudinally opposite sides of their associated leg cut-out.

7. The garment of claim 2 wherein the elastic second layer is a liquid-impervious material and extends beyond the crotch portion longitudinally of the garment.

8. The garment of claim 2 wherein the elasticized, gathered portion of the garment is extensible and contractible in the direction perpendicular of the longitudinal axis of the garment.

9. The garment of claim 2 wherein the elastic second layer comprises a nonwoven web of elastomeric fibers.

10. The garment of claim 2 wherein the elastic second layer comprises an elastomeric film.

11. The garment of claim 2 wherein the elastic second layer is stretch-bonded to the gatherable first layer at a plurality of spaced-apart locations in a repeating pattern and the gatherable first layer is gathered between the bonded locations.

12. The garment of claim 2 wherein the gatherable, non-elastic first layer is a liquid-pervious breathable material and the elastic second layer is a liquid-impervious material.

13. The garment of claim 12 further comprising a liquid-pervious, breathable third layer overlying the elastic second layer to provide a laminate in which the elastic second layer is sandwiched between the third layer and the first layer.

14. The garment of claim 12 further including an absorbent layer interposed between the third layer and the elastic second layer.

15. An incontinence control garment having a medial section which includes a crotch portion and is disposed between transversely opposed side sections which are contiguous with the medial section, the garment being comprised of a gatherable, non-elastic outer layer having a liquid-impervious elastic inner layer stretch-bonded thereto and overlying at least substantially the entire crotch portion of the garment to define an elasticized, liquid-impervious medial portion of the garment which is extensible and contractible in the direction transversely of the garment.

16. The garment of claim 15 wherein the crotch portion is defined between transversely opposed leg cut-outs and the transversely-opposed side sections each comprises a pair of side sub-sections respectively disposed on longitudinally opposite sides of their associated leg cut-outs.

17. The garment of claim 15 comprising a diaper of open, wrap-around construction.

18. The garment of claim 15 comprising a panty of closed, slip-on construction.

19. A method of producing a garment having a medial section which includes a gathered crotch portion and is disposed between transversely opposed side sections comprises:
    stretching an elastic second layer to elongate it;
    maintaining the elastic second layer in an elongated condition while bonding it to a gatherable first layer with the direction of elongation of the elastic layer positioned transversely of the garment to form a bonded composite material overlying at least the crotch portion of the garment; and
    relaxing the bonded composite material whereby to gather the gatherable, non-elastic first layer and form the gathered crotch portion.

20. The method of claim 19 wherein the gatherable first layer is a non-elastic layer.

21. The method of claim 20 wherein the gatherable, non-elastic first layer is a liquid-pervious, breathable material and the elastic second layer is a liquid-impervious material.

22. The method of claim 20 including stretching the elastic second layer to elongate it to an elongation of from about 10% to 600% of its relaxed length and maintaining such elongation while bonding the elastic second layer to the first layer.

23. The method of claim 20 including stretching the elastic second layer to an elongation of from about 50% to 300%.

* * * * *